US009386945B2

(12) United States Patent
Hostettler et al.

(10) Patent No.: US 9,386,945 B2
(45) Date of Patent: Jul. 12, 2016

(54) BLOOD LANCING DEVICE

(75) Inventors: Patrick Hostettler, Hasle-Rüegsau (CH); Aurelius Horisberger, Burgdorf (CH); Peter Stettler, Ersign (CH); Jurgen Wittmann, Burgdorf (CH); Chun-Mu Huang, Taichung (TW)

(73) Assignee: Bionime Corporation (TW)

( * ) Notice: Subject to any disclaimer, the term of this patent is extended or adjusted under 35 U.S.C. 154(b) by 555 days.

(21) Appl. No.: 13/618,065

(22) Filed: Sep. 14, 2012

(65) Prior Publication Data
US 2013/0190792 A1 Jul. 25, 2013

(30) Foreign Application Priority Data

Jan. 19, 2012 (TW) .............................. 101102196 A

(51) Int. Cl.
*A61B 17/32* (2006.01)
*A61B 5/15* (2006.01)
*A61B 5/151* (2006.01)

(52) U.S. Cl.
CPC ............ *A61B 5/1411* (2013.01); *A61B 5/15019* (2013.01); *A61B 5/1519* (2013.01); *A61B 5/150022* (2013.01); *A61B 5/15111* (2013.01); *A61B 5/15117* (2013.01); *A61B 5/150183* (2013.01); *A61B 5/15194* (2013.01); *A61B 5/150267* (2013.01); *A61B 5/150412* (2013.01)

(58) Field of Classification Search
CPC .. A61B 5/151; A61B 5/15117; A61B 5/1519; A61B 5/15194; A01B 12/006
USPC .......... 606/173, 181–186; 623/1.15; 600/583; 222/519–521, 549
See application file for complete search history.

(56) References Cited

U.S. PATENT DOCUMENTS

| 4,577,630 | A | * | 3/1986 | Nitzsche et al. | 606/182 |
| 5,613,978 | A | * | 3/1997 | Harding | 606/181 |
| 5,666,966 | A | * | 9/1997 | Horie et al. | 600/573 |
| 5,871,494 | A | * | 2/1999 | Simons et al. | 606/181 |
| 5,873,887 | A | * | 2/1999 | King et al. | 606/182 |
| 5,879,311 | A | * | 3/1999 | Duchon et al. | 600/583 |
| 5,916,230 | A | * | 6/1999 | Brenneman et al. | 606/172 |
| 5,951,493 | A | * | 9/1999 | Douglas et al. | 600/583 |
| 5,964,718 | A | * | 10/1999 | Duchon et al. | 600/583 |
| 6,045,567 | A | * | 4/2000 | Taylor et al. | 606/181 |
| 6,197,040 | B1 | * | 3/2001 | LeVaughn et al. | 606/182 |
| 6,558,402 | B1 | * | 5/2003 | Chelak et al. | 606/182 |
| 7,258,673 | B2 | * | 8/2007 | Racchini et al. | 600/583 |

(Continued)

FOREIGN PATENT DOCUMENTS

| EP | 0668049 B1 | 4/1999 |
| EP | 1204372 B1 | 7/2005 |

(Continued)

*Primary Examiner* — Amy R Weisberg
(74) *Attorney, Agent, or Firm* — Pepper Hamilton LLP

(57) ABSTRACT

A blood lancing device includes a housing unit and a cap. When the cap is disposed at an initial position, a second drive element is blocked by a first drive element from forward movement relative to the first drive element. When the cap is moved from the initial position to a retracted position, the first drive element pushes the second drive element so that the second drive element is deviated from the first drive element when a holder holding a lancet is moved to a trigger position, thereby allowing for a high speed movement of the holder from the trigger position to a pricking position by virtue of biasing action of a first biasing member.

23 Claims, 18 Drawing Sheets

(56) References Cited

U.S. PATENT DOCUMENTS

| | | | |
|---|---|---|---|
| 7,621,931 B2* | 11/2009 | Shraga | 606/182 |
| 8,801,740 B2* | 8/2014 | Koike et al. | 606/181 |
| 2001/0027327 A1* | 10/2001 | Schraga | 606/182 |
| 2002/0177787 A1* | 11/2002 | Duchon et al. | 600/583 |
| 2003/0050655 A1* | 3/2003 | Roe | 606/182 |
| 2003/0199892 A1* | 10/2003 | Kim | 606/181 |
| 2004/0068283 A1* | 4/2004 | Fukuzawa et al. | 606/181 |
| 2004/0073140 A1* | 4/2004 | Douglas et al. | 600/583 |
| 2004/0153034 A1* | 8/2004 | Fan | 604/197 |
| 2004/0162506 A1* | 8/2004 | Duchon et al. | 600/583 |
| 2005/0277849 A1* | 12/2005 | Wong et al. | 600/583 |
| 2006/0100655 A1* | 5/2006 | Leong et al. | 606/181 |
| 2006/0100656 A1* | 5/2006 | Olson et al. | 606/181 |
| 2007/0055298 A1* | 3/2007 | Uehata et al. | 606/181 |
| 2007/0233167 A1* | 10/2007 | Weiss et al. | 606/182 |
| 2009/0118753 A1* | 5/2009 | Dicesare et al. | 606/182 |
| 2009/0275860 A1* | 11/2009 | Nakamura et al. | 600/573 |
| 2009/0281459 A1* | 11/2009 | Faulkner et al. | 600/583 |
| 2010/0036318 A1* | 2/2010 | Raday et al. | 604/134 |
| 2010/0094324 A1* | 4/2010 | Huang et al. | 606/182 |
| 2010/0121366 A1* | 5/2010 | Weiss et al. | 606/172 |
| 2011/0245635 A1* | 10/2011 | Fujiwara et al. | 600/309 |
| 2012/0157965 A1* | 6/2012 | Wotton et al. | 604/506 |
| 2013/0158586 A1* | 6/2013 | Pusey et al. | 606/173 |
| 2013/0172920 A1* | 7/2013 | Euteneuer et al. | 606/185 |
| 2013/0204162 A1* | 8/2013 | Saeki et al. | 600/583 |
| 2013/0237905 A1* | 9/2013 | Holmqvist | 604/89 |
| 2013/0267978 A1* | 10/2013 | Trissel | 606/182 |
| 2013/0324886 A1* | 12/2013 | Fu | 600/576 |
| 2014/0058428 A1* | 2/2014 | Christopher et al. | 606/182 |
| 2014/0074138 A1* | 3/2014 | Kan | 606/182 |
| 2014/0214065 A1* | 7/2014 | Kim | 606/172 |

FOREIGN PATENT DOCUMENTS

| | | |
|---|---|---|
| EP | 1247489 B1 | 6/2007 |
| EP | 1755456 B1 | 10/2009 |
| EP | 2050393 B1 | 4/2011 |
| WO | WO2008/009985 A1 | 1/2008 |
| WO | WO2010/098531 A1 | 9/2010 |

\* cited by examiner

BLOOD LANCING DEVICE

CROSS-REFERENCE TO RELATED APPLICATION

This application claims priority of Taiwanese Application No. 101102196, filed on Jan. 19, 2012.

BACKGROUND OF THE INVENTION

1. Field of the Invention

The invention relates to a blood lancing device for pricking a person's skin to obtain a drop of blood.

2. Description of the Related Art

Many medical procedures require a relatively small sample of blood, in the range of 5-50 μl. Normally such a sample is obtained by lancing or piercing the skin at a selected location, such as a finger, to enable collection of 1 or 2 drops of blood. With the advancement of home use tests such as self monitoring of blood glucose, there is a requirement for a simple and safe procedure which can be performed by a person needing such tests.

Lancets in conventional use generally have a rigid body and a sterile pricking element, for example a needle, which protrudes from one end of the rigid body to pierce the skin, thereby enabling the collection of the blood sample. The collected blood is then transferred to a test device or a collection device. Blood is most commonly taken from fingertips, where the supply is generally excellent. However, blood can also be taken from alternate sites, such as earlobes and limbs.

To reduce the anxiety of piercing the skin and to guarantee a reproducible penetration result, many spring-loaded lancing devices have been developed. For example, a lancing device disclosed in European Patent No. 2050393 includes a mode-switch member for switching the lancing device between a cocking state, wherein operation of a loading member provides a cocking of a lancet holder, and a firing state, wherein further operation of the loading member provides an ejection of a lancet placed in the lancet holder.

The abovementioned operations of the loading member need to be done manually. However, the size of such a lancing device is relatively small, so that these manual operations are difficult to be performed on the miniature lancing device.

In another conventional lancing device disclosed in European Patent No. 0668049, before firing, a drive spring is compressed such that a biasing force of the drive spring is sufficient to cause a plunger to strike and drive a lancet into a user's finger. As such, safety can be promoted. However, many manual operations are still required during the lancing process.

In yet another conventional lancing device disclosed in U.S. Pat. No. 4,577,630, a mechanical trigger mechanism can be activated by a contact pressure between the patient's skin and the mechanical trigger mechanism.

In a single-use skin pricking device disclosed in European Patent No. 1247489, a trigger is releasably coupled to a lancet such that movement of the trigger in a first direction moves the lancet in a direction to compress a biasing means, and then causes release of the lancet from the trigger whereby the biasing means drives the lancet in a second direction substantially opposite to the first direction.

In European Patent No. 1755456, a lancet device includes a housing and a lancet structure having a puncturing element. The lancet structure is disposed within the housing and is adapted for movement between a retaining or pre-actuated position where the puncturing element is retained within the housing, and a puncturing position where the puncturing element extends through a forward end of the housing. The lancet device further includes a drive spring disposed within the housing for biasing the lancet structure toward the puncturing position, and a retaining hub retaining the lancet structure in the retaining position against the bias of the drive spring. The retaining hub includes a pivotal lever in interference engagement with the lancet structure. An actuator within the housing pivots the lever, thereby moving the lancet structure toward the rearward end of the housing to at least partially compress the drive spring, and releasing the lever from interference engagement with the lancet structure. Such a lancet device is disposable after a single use, and thus is suitable for hospital applications. However, it is necessary for a diabetic patient to carry a plurality of the disposable lancet devices, thereby resulting in inconvenience during use.

In skin pricking devices disclosed in WO 2008/009985, WO2010/098531, and European Patent No. 1204372, a spring can be preloaded prior to assembly of the device. However, these devices are also disposable after a single use, and are operated by manual firing. Hence, it is desirable that a plurality of skin pricking operations can be performed by repeated depressions of the lancing device.

SUMMARY OF THE INVENTION

Therefore, the object of the present invention is to provide a blood lancing device that can perform a plurality of skin pricking operations by repeated presses of the lancing device.

Accordingly, a blood lancing device of the present invention is adapted for pricking a person's skin to obtain a drop of blood and comprises:

a housing unit including a housing body and a positioning portion that is disposed in the housing body, the housing body having a front end section and a rear end section that is opposite to the front end section along an axis;

a cap projecting forwardly from the housing unit, and movable relative to the housing body along the axis between an initial position and a retracted position, the cap having a front end that is disposed outwardly of the housing unit, that is adapted to be in contact with the skin, and that has an opening;

a lancet;

a holder disposed in the housing unit between the cap and the positioning portion of the housing unit, holding the lancet, and movable along the axis relative to the housing unit between a pricking position whereat the lancet extends outwardly from the opening of the cap, and a trigger position whereat the lancet as a whole is disposed in the housing unit;

a first biasing member disposed between the holder and the positioning portion of the housing unit for biasing the holder to move along the axis away from the positioning portion of the housing unit; and a transmission assembly including a first drive element that is disposed between the cap and the holder and that is driven movably along the axis by the cap, and at least one second drive element that is aligned with the first drive element in the direction of the axis and that is disposed fixedly on the holder such that, when the cap is moved from the initial position toward the retracted position, the second drive element is blocked by the first drive element from forward movement to maintain relative positions of the holder and the first drive element so that the first drive element pushes the holder toward the trigger position and that the second drive element is deviated from the first drive element when the holder reaches the trigger position, thereby allowing for a high speed movement of the holder from the trigger position to the pricking position by virtue of biasing action of the first biasing member.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
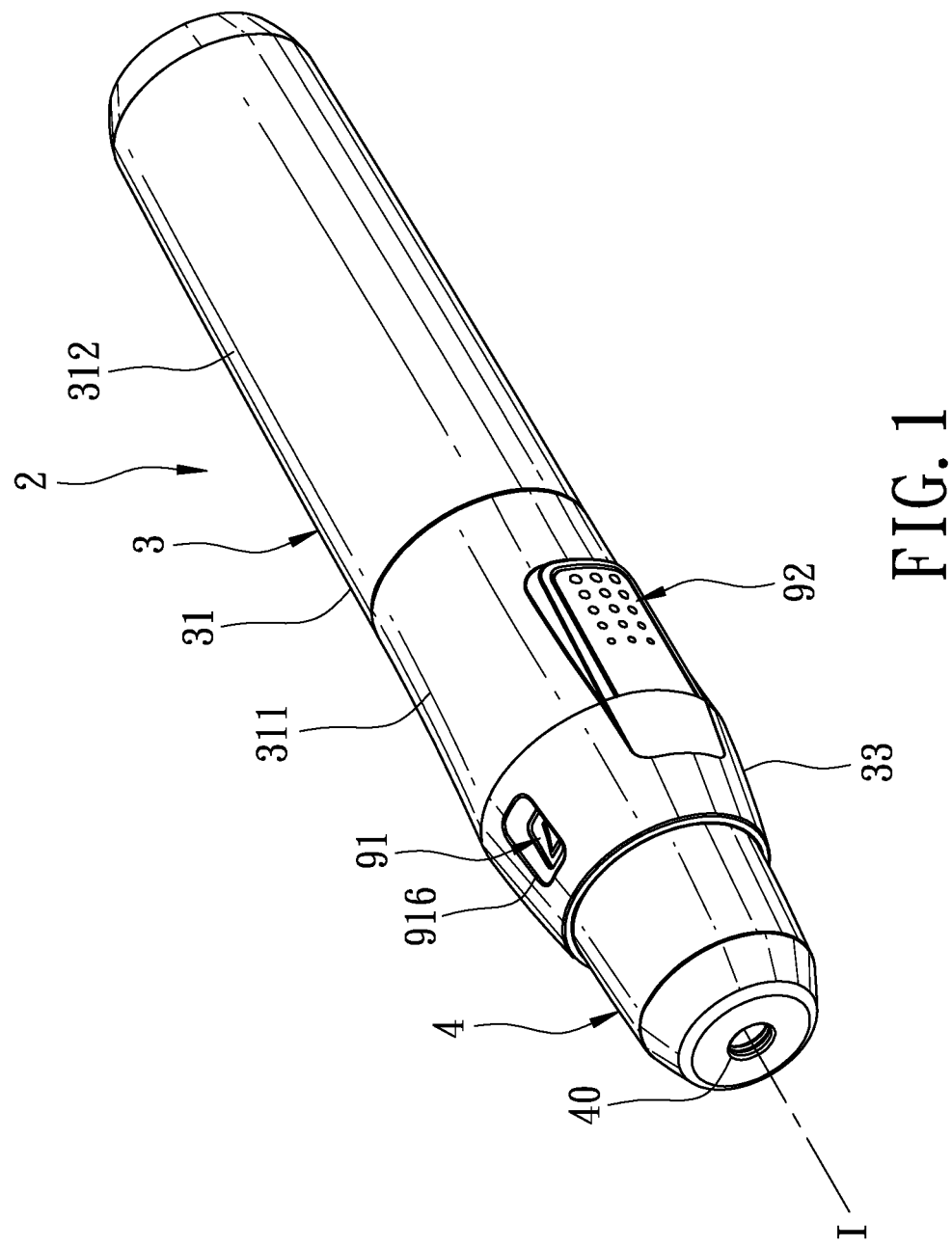
FIG. 1 is a perspective view of a preferred embodiment of a blood lancing device according to the invention, illustrating a cap at an initial position.
Figure 3:
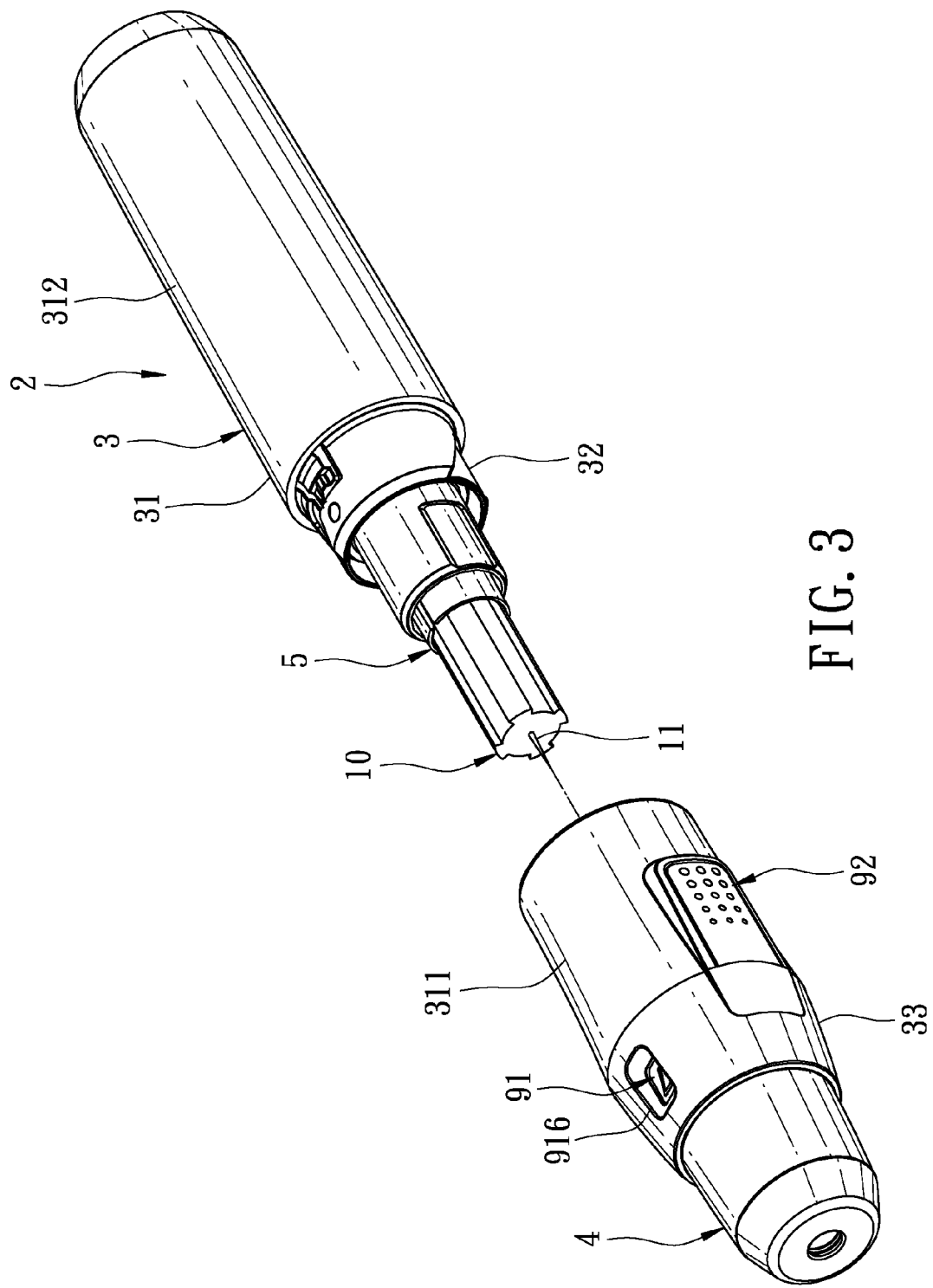
FIG. 3 is a partly exploded view of the preferred embodiment.
Figure 5:
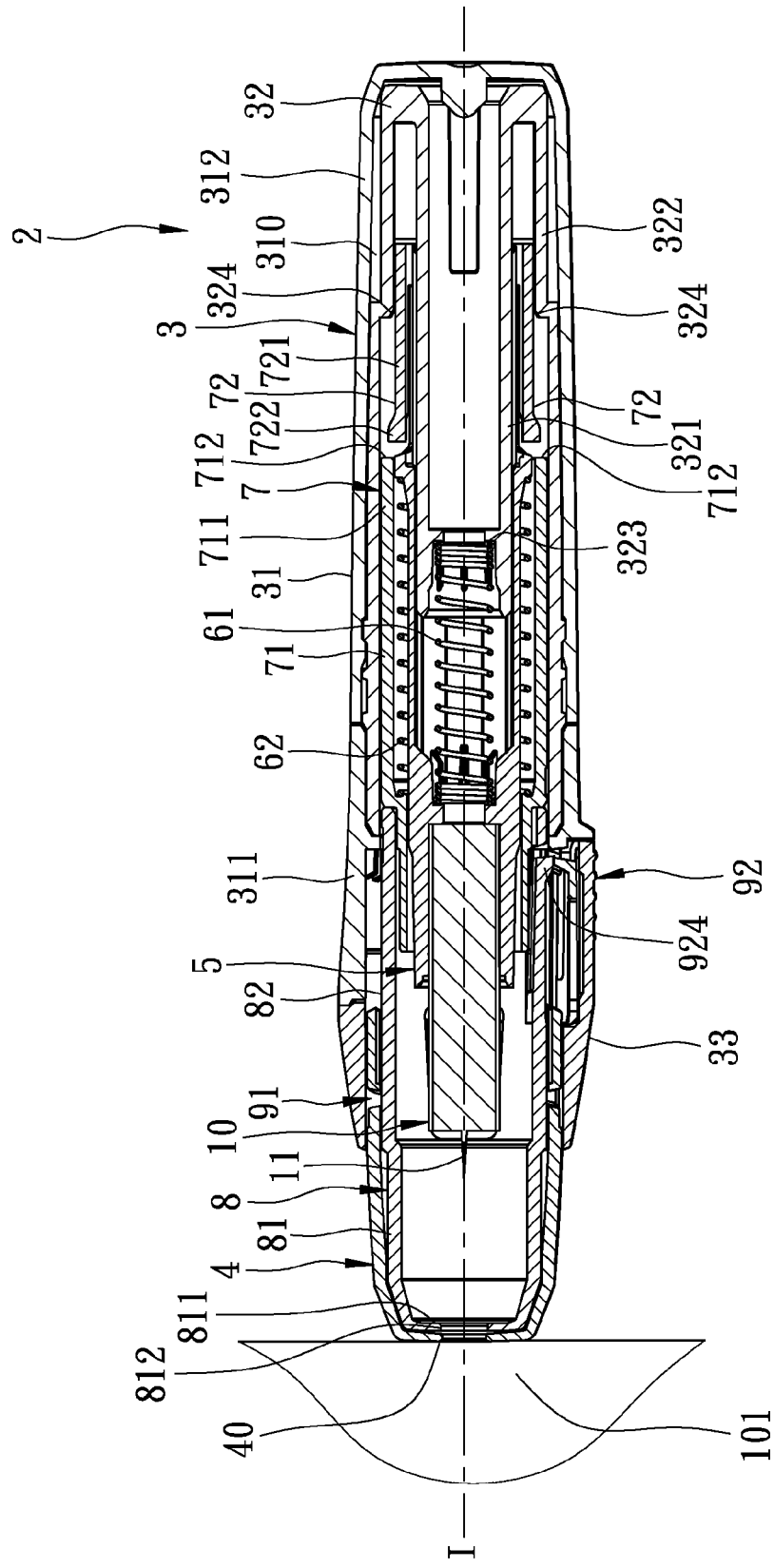
FIG. 5 is a sectional view of the preferred embodiment, illustrating the cap at the initial position and a holder of the preferred embodiment at a pre-actuated position.

As shown in FIGS. 1, 3 and 5, a preferred embodiment of a blood lancing device 2 according to the present invention is adapted for pricking a person's skin 101 to obtain a drop of blood. The blood lancing device 2 comprises a housing unit 3, a cap 4 disposed movably on the housing unit 3, a lancet 10, a holder 5 disposed between the housing unit 3 and the cap 4 and holding the lancet 10, a first biasing member 61 disposed between the holder 5 and the housing unit 3, a transmission assembly 7 disposed between the cap 4 and the holder 5, a sleeve unit 8 disposed between the cap 4 and the transmission assembly 7, a pair of angularly spaced-apart adjusting units 91 (only one is shown) disposed between the sleeve unit 8 and the cap 4, a safety switch 92 disposed between the housing unit 3 and the sleeve unit 8, and a second biasing member 62 disposed between the holder 5 and the transmission assembly 7. In this embodiment, the first and second biasing member 61, 62 are configured as coil springs, but are not limited to such.

The housing unit 3 includes a housing body 31 that surrounds an axis (I) and that defines a retaining space 310, and a positioning member 32 that is retained in the retaining space 310. In this embodiment, the housing body 31 is tubular and is easy to be manufactured and to be held by a user. The housing body 31 has a front end section 311 that is adapted to be placed proximate to the skin 101 when the blood lancing device 2 is in use, and a rear end section 312 that is opposite to the front end section 311 along the axis (I) and that is adapted to be placed distal from the skin 101. The positioning member 32 has inner and outer wall segments 321, 322 that surround the axis (I). The inner wall segment 321 has a positioning portion 323 for abutting against an end of the first biasing member 61. The outer wall segment 322 has a pair of angularly spaced-apart cam surfaces 324 that face the cap 4. The housing body 31 and positioning member 32 may be molded as one piece.

Figure 2:
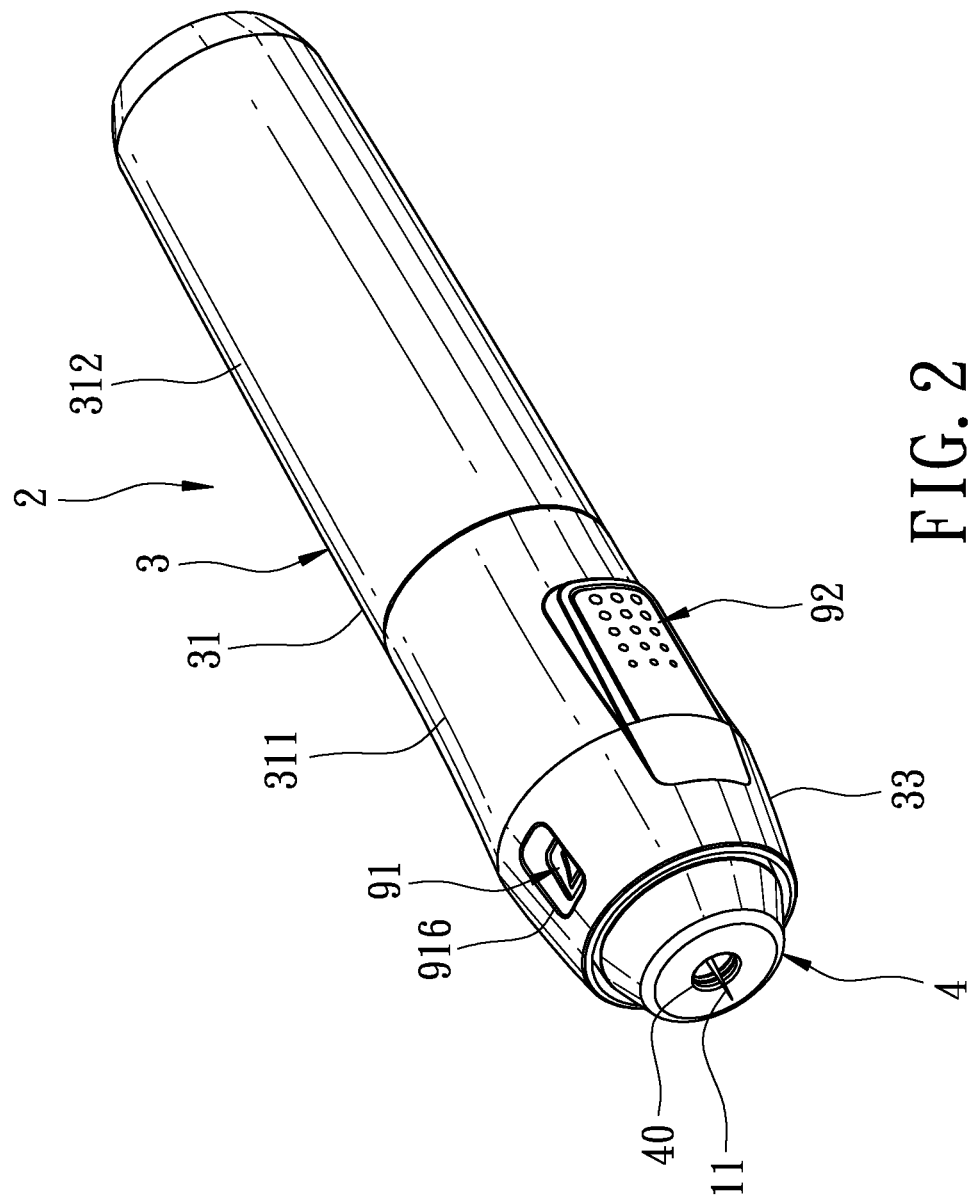
FIG. 2 is another perspective view of the preferred embodiment, illustrating the cap at a retracted position.

The cap 4 projects forwardly from a front end of the housing unit 3, and is movable relative to the housing body 31 along the axis (I) between an initial position (see FIG. 1) and a retracted position (see FIG. 2). The cap 4 has a front end wall that is disposed outwardly of the housing unit 3, that is adapted for contact with the skin 101, and that has an opening 40.

Figure 18:
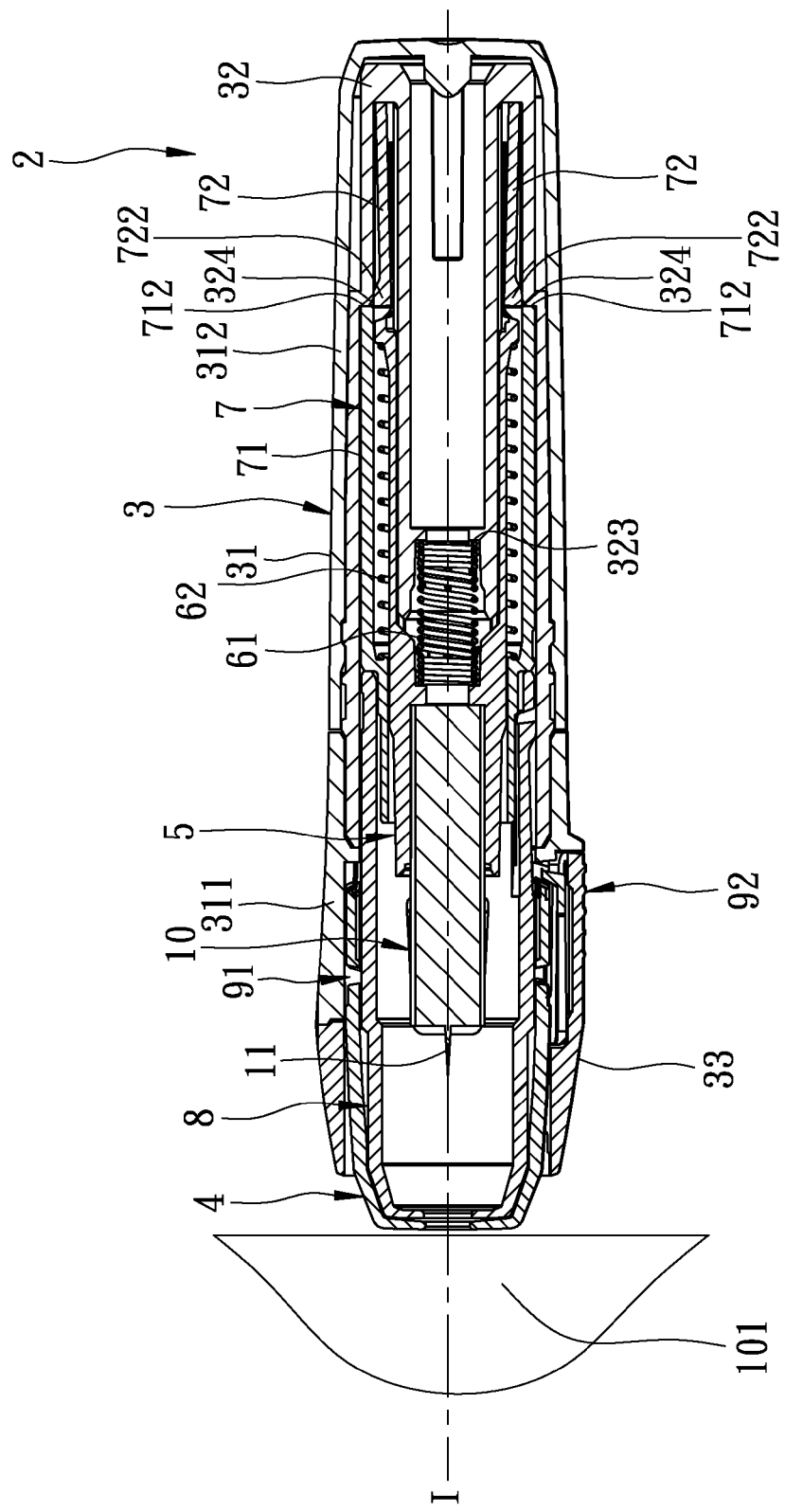
FIG. 18 is another sectional view of the preferred embodiment, illustrating the cap at the retracted position and the holder at a trigger position

The holder 5 is disposed between the cap 4 and the positioning portion 323 of the positioning member 32 of the housing unit 3, and is movable along the axis (I) relative to the housing unit 3 between a pricking position (see FIG. 7) where a needle 11 of the lancet 10 extends outwardly from the opening 40 of the cap 4, and a trigger position (see FIG. 18) where the lancet 10 as a whole is disposed in the housing unit 3.

The first biasing member 61 is disposed between the holder 5 and the positioning portion 323 of the housing unit 3 for biasing the holder 5 to move along the axis (I) away from the positioning portion 323 of the housing unit 3.

The transmission assembly 7 includes a first drive element 71 that is connected between the cap 4 and the holder 5 and that is driven movably along the axis (I) by the cap 4, and a pair of second drive elements 72 that are aligned with the first drive element 71 in the direction of the axis (I), that correspond respectively in position to the cam surfaces 324 of the housing unit 3, and that are disposed fixedly on the holder 5 such that, when the cap 4 is moved from the initial position toward the retracted position, the second drive elements 72 are blocked by the first drive element 71 from forward movement to maintain relative positions of the holder 5 and the first drive element 71 so that the first drive element 71 pushes the holder 5 toward the trigger position and that the second drive elements 72 are deviated from the first drive element 71 when the holder 5 reaches the trigger position, thereby allowing for a high speed movement of the holder 5 from the trigger position to the pricking position by virtue of biasing action of the first biasing member 61. In this embodiment, the first drive element 71 and the cap 4 are two individual parts. The first drive element 71 is tubular, is disposed between the cap 4 and the holder 5 and is movable in the housing unit 3.

Figure 4:
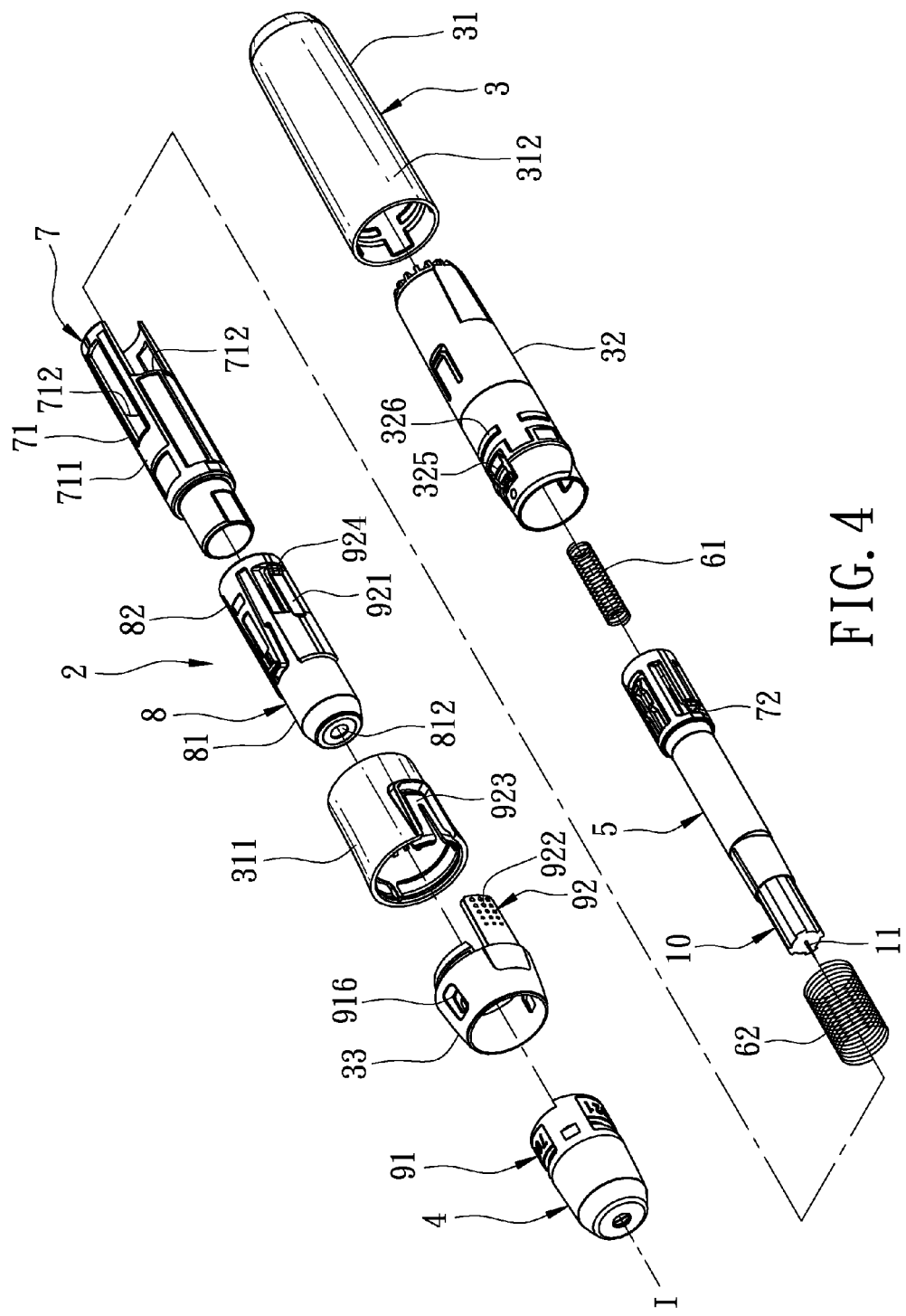
FIG. 4 is an exploded view of the preferred embodiment.
Figure 8:
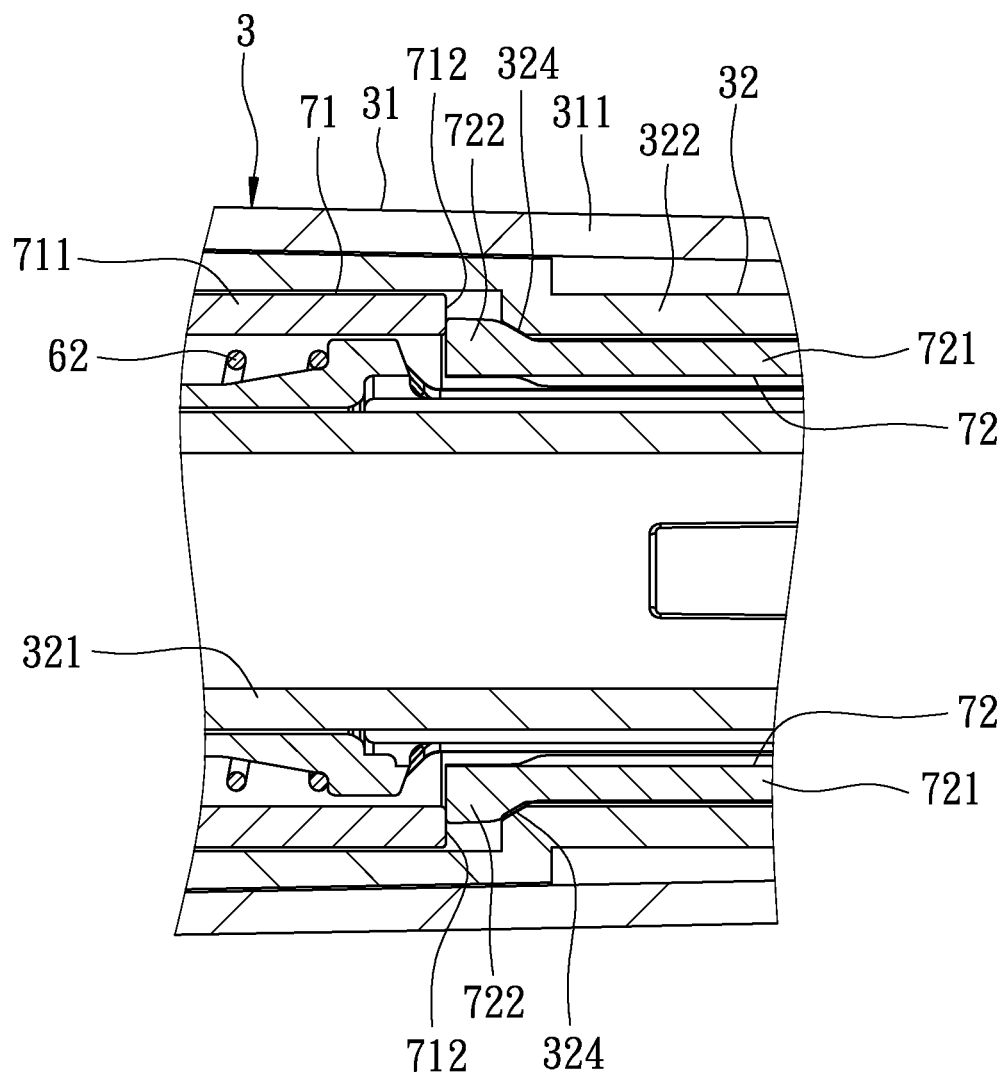
FIG. 8 is an enlarged fragmentary sectional view of the preferred embodiment, illustrating the relation between first and second drive elements of a transmission assembly and a cam surface of a housing unit.
Figure 9:
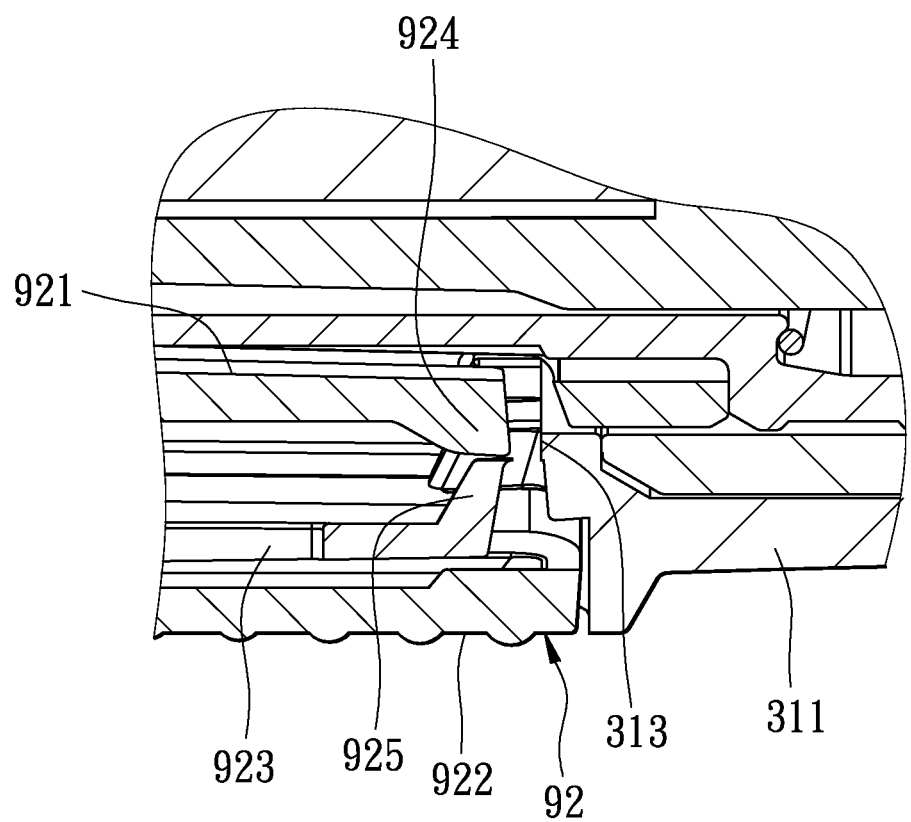
FIG. 9 is another enlarged fragmentary sectional view of the preferred embodiment, illustrating a flexible rod and a pressing lever of a safety switch, and a stop surface of a front end section of the housing unit.

As shown in FIGS. 4, 5 and 8, each of the second drive elements 72 has a flexible and elongated rod portion 721 extending forwardly from a rear portion of the holder 5, and a cam block 722 disposed on a front free end of the rod portion 721. The first drive element 71 has a main body 711 and a pair of limiting surfaces 712 disposed at a rear end of the main body 711 and facing respectively the cam surfaces 324 of the housing unit 3. The second drive elements 72 are configured such that, when the cap 4 drives the first drive element 71 to move from the initial position toward the retracted position, the limiting surfaces 712 of the first drive element 71 abut respectively against the cam blocks 722 of the second drive elements 72 for preventing the forward movement of the second drive elements 72 along the axis (I) relative to the first drive element 71. When the first drive element 71 pushes the second drive elements 72 to reach a cocking position (see FIG. 6), the cam blocks 722 of the second drive elements 72 come into contact with the cam surfaces 324. With a further movement of the second drive elements 72 from the cocking position to the trigger position, the second drive elements 72 are urged by the cam surfaces 324 to deform inwardly and to deviate from the limiting surfaces 712 of the first drive element 71 so that the second drive elements 72 and the holder 5 prick toward the cap 4 along the axis (I) by virtue of the first biasing member 61.

It is noted that the blood lancing device 2 of this invention may comprise only one second drive element 72, one limiting surface 712 on the first drive element 71 corresponding to the one second drive element 72, and one cam surface 324 on the positioning member 32 of the housing unit 3 corresponding to the one second drive element 72. Moreover, each of the cam surface 324 and the limiting surface 712 may be annular or the like.

Figure 10:
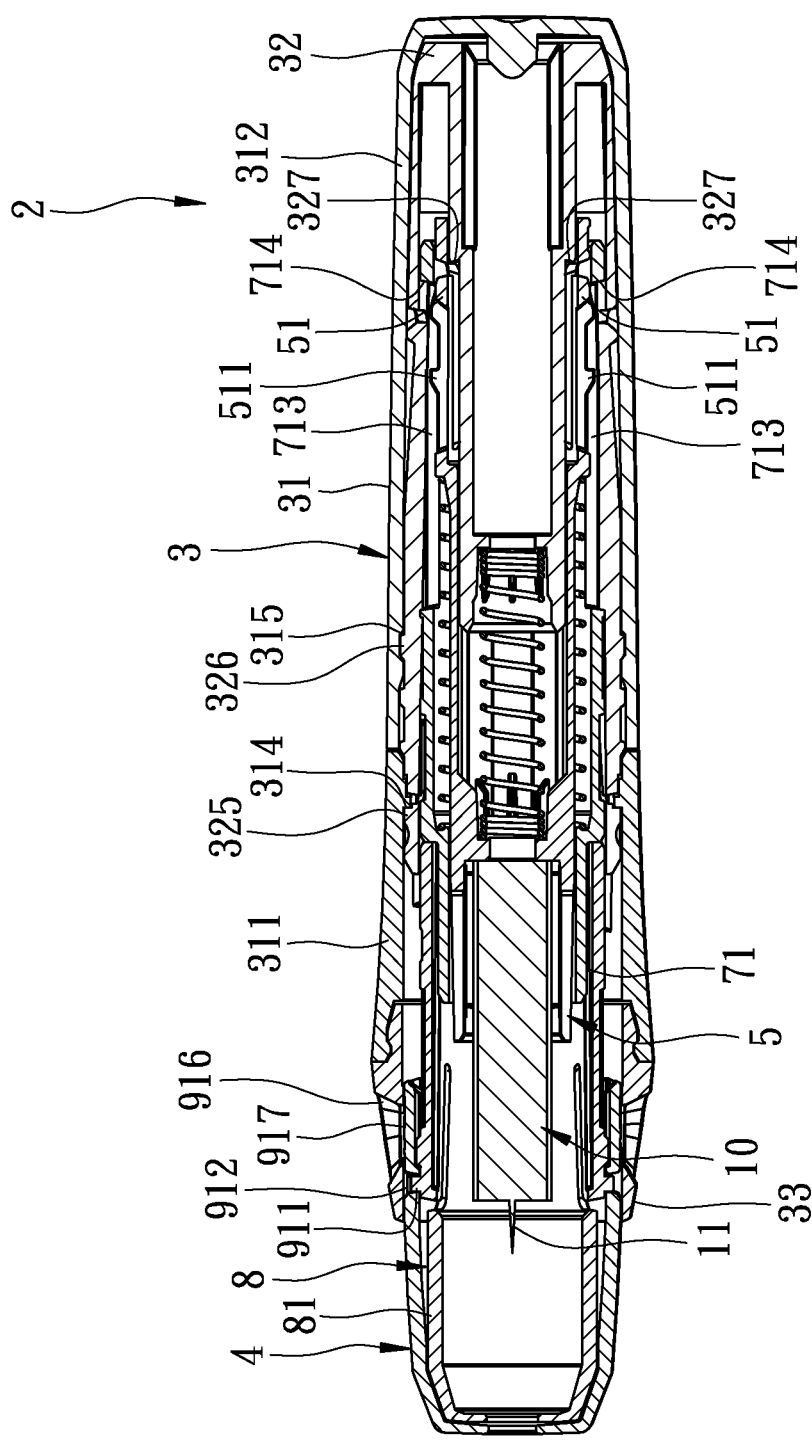
FIG. 10 is still another sectional view of the preferred embodiment, illustrating the relation between a flexible end portion of the holder and an abutment surface of the housing unit at the pre-actuated position.

As shown in FIGS. 4 and 10, in this embodiment, the front end section 311 and the rear end section 312 of the housing body 31 are interconnected removably for facilitating the assembly of the blood lancing device 2. The positioning member 32 is formed with first and second engaging portions 325, 326 corresponding respectively to the front and rear end sections 311, 312. The front end section 311 has an inner surrounding surface formed with an engaging part 314 for engaging removably the first engaging portion 325 of the positioning member 32. The rear end section 312 has an inner surrounding surface formed with an engaging part 315 for engaging the second engaging portion 326 of the positioning member 32. After assembly, each of the holder 5, the first biasing member 61, and the first drive element 71 has a majority retained in the rear end section 312, while the cap 4 is disposed adjacent to the front end section 311. In addition to interconnect the front and rear end sections 311, 312, the positioning member 32 may be further formed with other structures for facilitating the assembly of other elements.

Figure 7:
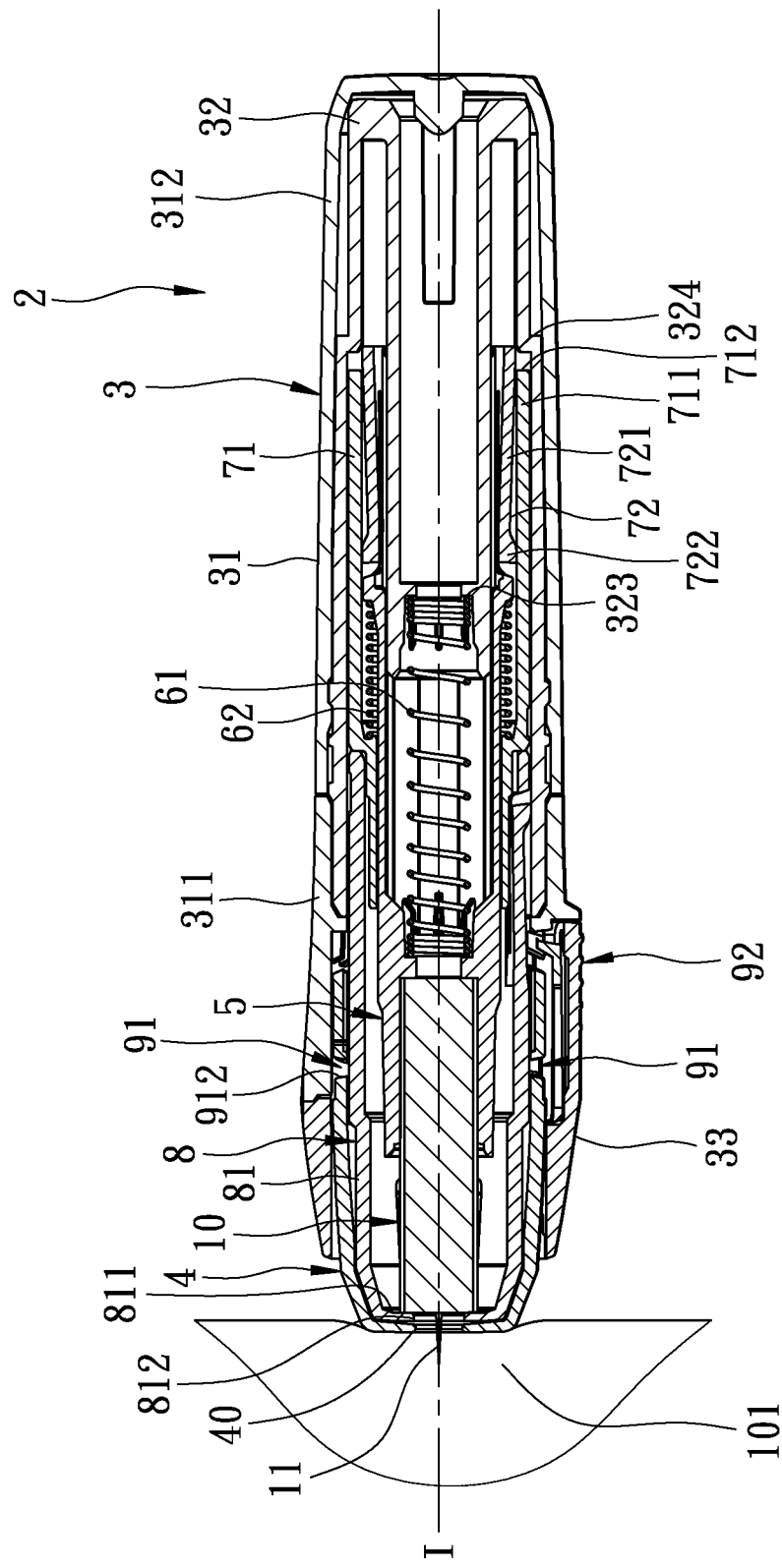
FIG. 7 is still another sectional view of the preferred embodiment, illustrating the cap at the retracted position and the holder at a pricking position.
Figure 13:
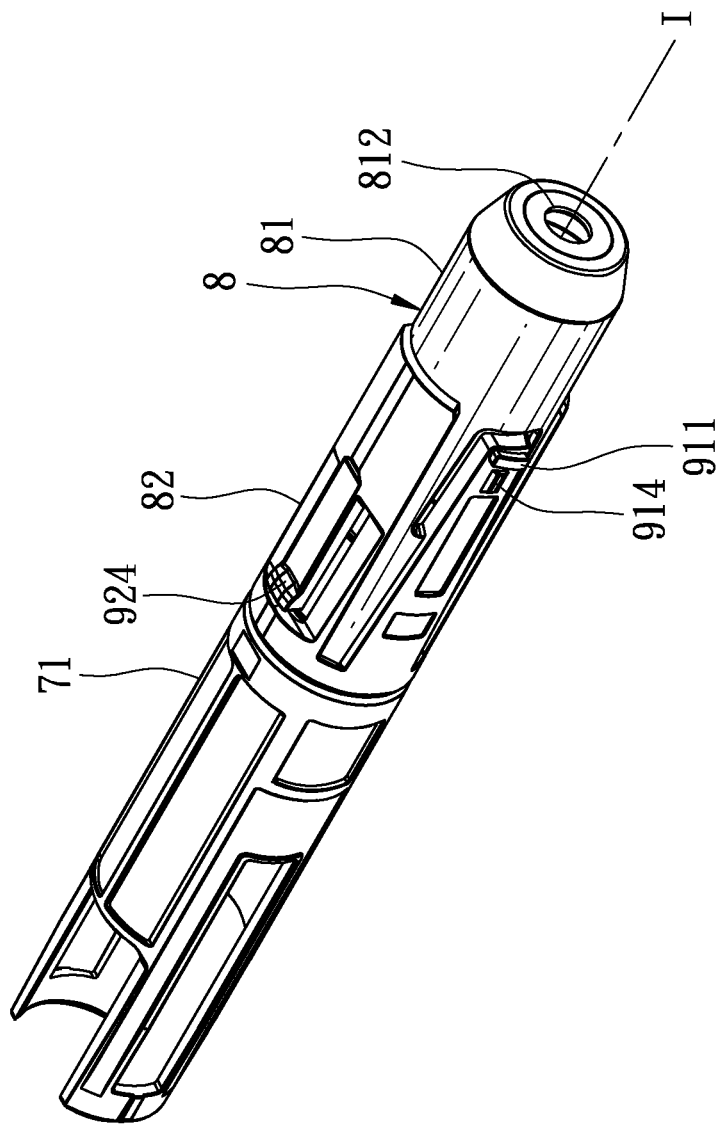
FIG. 13 is a perspective view illustrating a connection between a sleeve unit and the first drive element of the preferred embodiment.
Figure 14:
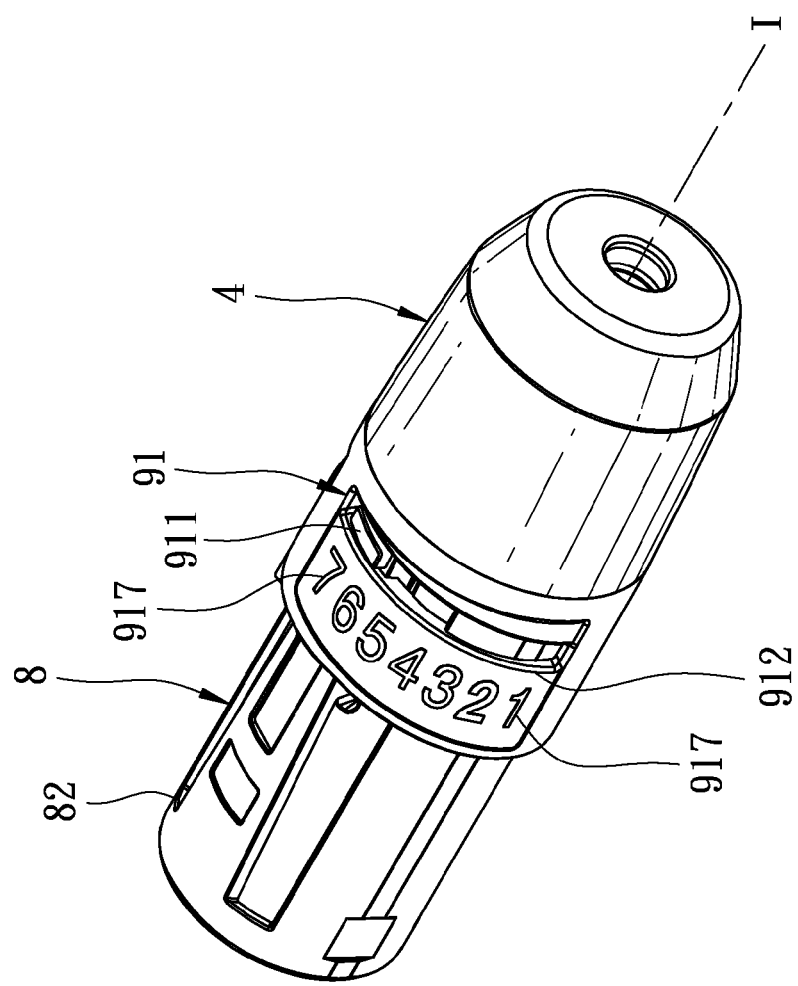
FIG. 14 is a perspective view illustrating a connection between the sleeve unit and the cap of the preferred embodiment.

Referring to FIGS. 7, 13 and 14, the sleeve unit 8 abuts against the first drive element 71 and is driven by the cap 4 to move along the axis (I) relative to the housing unit 3. The holder 5 is retained in and is movable along the axis (I) relative to the sleeve unit 8. The sleeve unit 8 includes a stopper 81 and a sleeve body 82 respectively proximate to and distal from the cap 4. In this embodiment, the sleeve body 82 and the stopper 81 are formed integrally.

Figure 16:
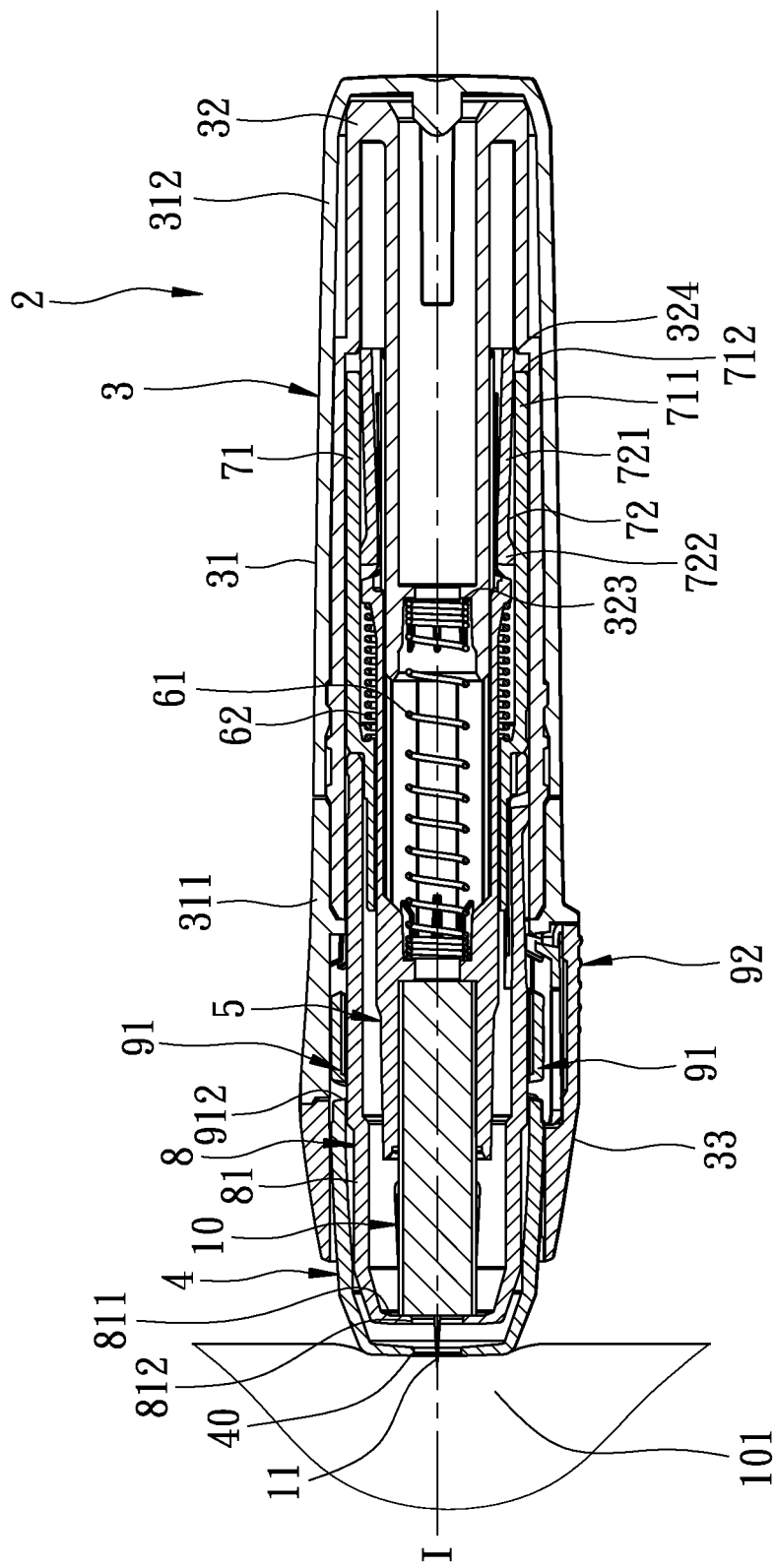
FIG. 16 is yet another sectional view of the preferred embodiment after adjustment of a distance between the cap and the sleeve unit.
Figure 17:
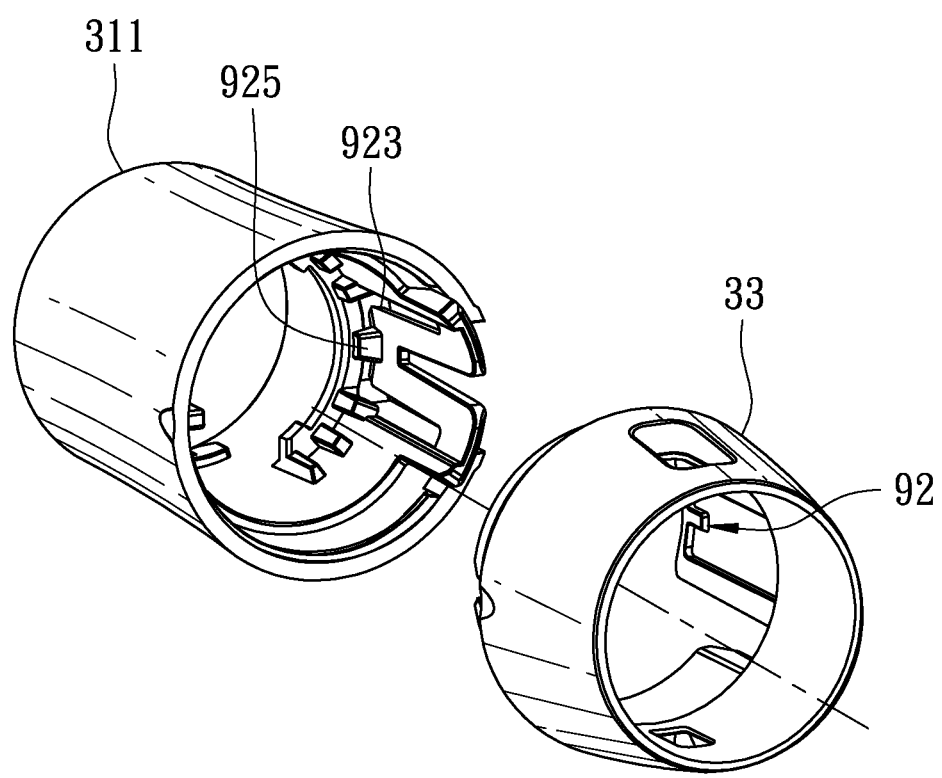
FIG. 17 is an exploded perspective view of an end piece and the front end section of the housing unit of the preferred embodiment.

The stopper 81 has a front end wall 811 contactable with the lancet 10 for preventing further forward movement of the lancet 10, and an aperture 812 formed through the front end wall 811 and aligned with the opening 40 in the cap 4 along the axis (I). The lancet 10 includes an insert body held by the holder 5 and movable to come into contact with the front end wall 811 of the stopper 81 when the holder 5 is disposed at the pricking position, and a needle 11 mounted fixedly on a front end of the insert body and extending through the opening 40 and the aperture 812 when the holder 5 is disposed at the pricking position. The cap 4 is movable along the axis (I) relative to the stopper 81 to change the distance between the front end wall 811 of the stopper 81 and the front end wall of the cap 4, thereby adjusting the length of a portion of the needle 11 projecting out of the cap 4 (see FIG. 7 and FIG. 16).

Figure 15:
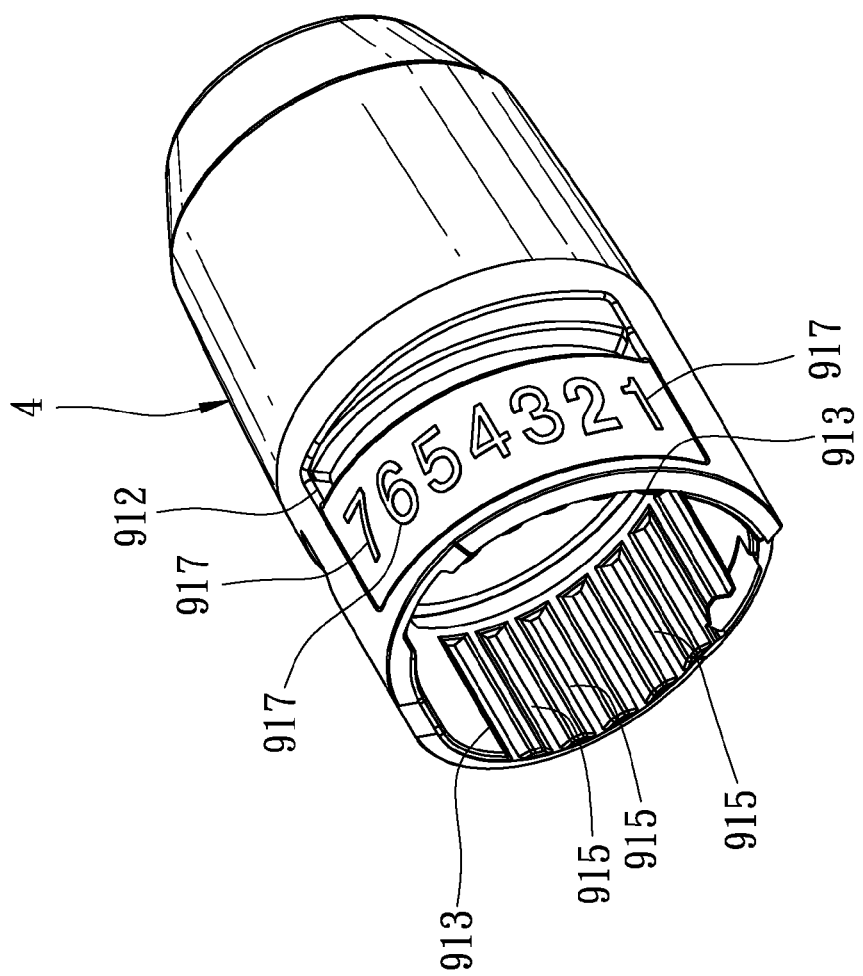
FIG. 15 is a perspective view of the cap of the preferred embodiment.

Referring to FIGS. 13, 14 and 15, the adjusting units 91 are disposed between the stopper 81 and the cap 4. Each of the adjusting units 91 includes a guide block 911 disposed on the stopper 81, an inclined spirally-extending guide slot 912 formed in the cap 4 and slideably engaged with the guide block 911, an engaging tooth 914 disposed on an outer surface of the stopper 81, and a positioning portion 913 having a plurality of circumferentially arranged positioning grooves 915 formed in an inner surface of the cap 4. The cap 4 is rotatable relative to the stopper 81 and movable along the axis (I) relative to the stopper 81 through engagement between the guide block 911 and the guide slot 912 so as to change the distance between the front end wall of the cap 4 and the front end wall 811 of the stopper 81. The engaging tooth 914 is engagable with a selected one of the positioning grooves 915 to position the cap 4 relative to the stopper 81. To aid turning the cap 4 relative to the stopper 81, a restricting structure is formed between the sleeve unit 8 and the housing unit 3 such that the sleeve unit 8 cannot rotate but can move axially relative to the housing unit 3.

It should be noted that, while this invention is exemplified using a pair of adjusting units 91, only one adjusting unit 91 may be employed in other embodiments of this invention.

Referring to FIGS. 1, 14 and 15, preferably, the housing unit 3 further includes an end piece 33 connected to the front end section 311 of the housing body 31 and disposed around the cap 4. Each of the adjusting units 91 further includes a window 916 formed in the end piece 33, and a plurality of marks 917 disposed on an outer surface of the cap 4 and corresponding respectively to the positioning grooves 915 of the corresponding one of the adjusting units 91 such that rotation of the cap 4 relative to the end piece 33 results in an individual exposure of the marks 917 through the window 916, thereby indicating an adjusted a length of a portion of the needle 11 of the lancet 10 extending outwardly from the opening 40 of the cap 4 when the holder 5 is at the pricking position.

The marks 917 may be configured as symbols or numerals and each of which indicates a respective length of the needle 11 of the lancet 10 extending outwardly from the opening 40 of the cap 4 when the holder 5 is at the pricking position. In this embodiment, the marks 917 are configured as numerals. As shown in FIGS. 10 and 14, for each adjusting unit 91, when the guide block 911 is at an end of the guide slot 912 proximate to the opening 40, the numeral "7" of the marks 917 is exposed through the window 916, and the cap 4 is positioned relative to the stopper 81 through the engagement between the engaging tooth 914 and a corresponding positioning groove 915. As such, the front end wall 811 of the stopper 81 is at a closest position relative to the opening 40 of the cap 4, thereby resulting in a maximum length of the portion of the needle 11 projecting out of the cap 4 when the holder 5 is at the pricking position. On the contrary, when the guide block 911 is at another end of the guide slot 912 distal from the opening 40 and the numeral "1" of the marks 917 is exposed through the window 916, the front end wall 811 of the stopper 81 is at a farthest position relative to the opening 40 in the cap 4, thereby resulting in a minimum length of the portion of the needle 11 projecting out of the cap 4 when the holder 5 is at the pricking position.

Referring to FIGS. 4, 5, 9 and 17, the safety switch 92 is disposed between the end piece 33 of the housing unit 3 and the sleeve body 82 of the sleeve unit 8, and is operable for preventing an unexpected movement of the cap 4 relative to the housing body 31 from the initial position to the retracted position that causes a triggering action of the device. The front end section 311 of the housing unit 3 has a stop surface 313 that faces the cap 4. The safety switch 92 includes a flexible rod 921 connected to and co-movable with the sleeve body 82, and abutting against the stop surface 313 so as to prevent movement of the cap 4 from the initial position to the retracted position. The safety switch 92 further includes a pressing lever 922 disposed on and formed integrally with the end piece 33, and a flexible driven portion 923 connected to the front end section 311 and disposed between the flexible rod 921 and the pressing lever 922. The flexible rod 921 has a rear free end formed with a projection 924 projecting toward the flexible driven portion 923. The flexible driven portion 923 has a rear free end formed with a projection 925 projecting toward the projection 924 of the flexible rod 921. The pressing lever 922 is operable to push the flexible rod 921 to deviate from the stop surface 313 of the front end section 311 via the contact between the pressing lever 922 and the flexible driven portion 923 and the contact between the projection 925 of the flexible driven portion 923 and the projection 924 of the flexible rod 921, thereby allowing the movement of the cap 4 from the initial position to the retracted position. Therefore, an unexpected pricking action may be prevented.

It is noted that, in other embodiments, the sleeve unit 8 may be omitted to result in a constant pricking length of the needle 11 of the lancet 10 outwardly of the cap 4, and the flexible rod 921 of the safety switch 92 may hence be connected directly to the cap 4 to prevent the unexpected pricking action of the device.

Figure 11:
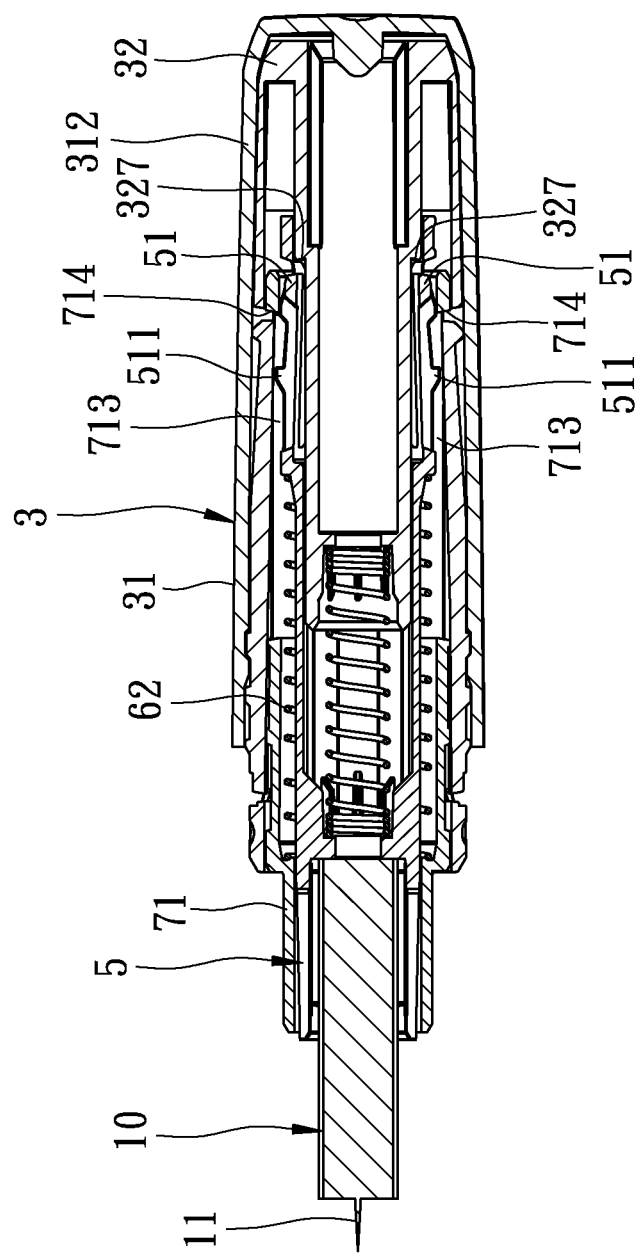
FIG. 11 is still another sectional view of the preferred embodiment, illustrating the flexible end portion deformed after removal of the front end section of the housing unit so that the holder is blocked from moving rearwardly.
Figure 12:
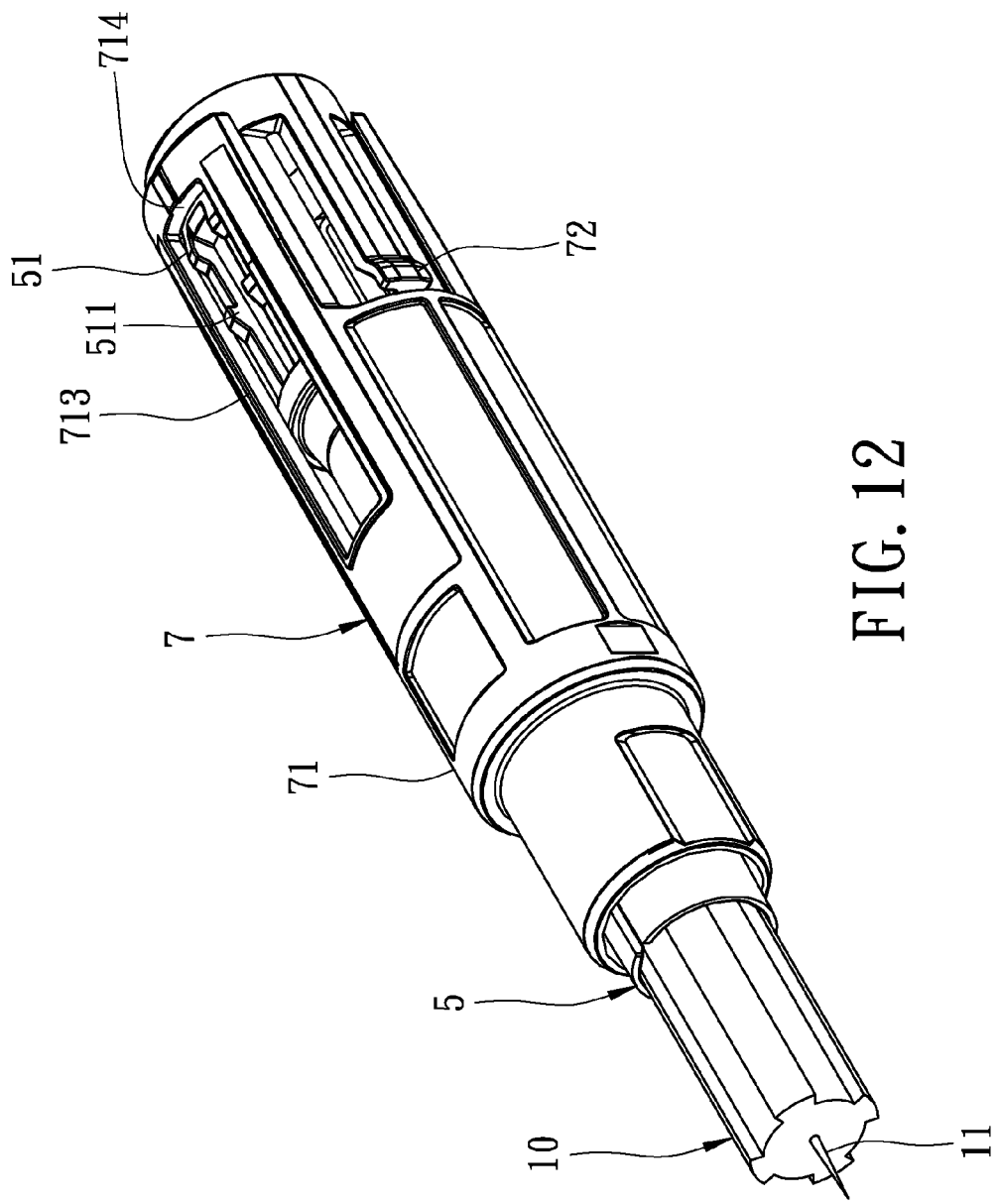
FIG. 12 is a perspective view illustrating the relation between the transmission assembly and the holder of the preferred embodiment.

Referring to FIGS. 10, 11 and 12, the second biasing member 62 is disposed between the holder 5 and the first drive element 71 of the transmission assembly 7 for biasing the holder 5 and the first drive element 71 to move away from each other. To replace the lancet 10 after use, the front end section 311 needs to be removed from the positioning member 32, and the sleeve unit 8 and the cap 4 need to be removed from the first drive element 71 of the transmission assembly 7. Afterward, the first drive element 71 is pushed to move to an advanced position (see FIG. 11) relative to the holder 5 by the second biasing member 62.

Preferably, the holder 5 has a pair of flexible end portions 51 angularly spaced apart from each other and staggered with the second drive elements 72. The first drive element 71 is formed with a pair of receiving holes 713 receiving respectively the flexible end portions 51 of the holder 5. Each of the receiving holes 713 is defined by a surface unit that has a restricting surface 714 facing the cap 4. The inner wall segment 321 of the positioning member 32 of the housing unit 3 further has a pair of abutment surfaces 327 corresponding to and deviated from the flexible end portions 51 of the holder 5, respectively. The abutment surfaces 327 are positioned such that, when the front end section 311 is removed and the first drive element 71 is pushed to the advanced position, the first drive element 71 is biased by the second biasing member 62 to move forward relative to the holder 5 and bring the flexible end portions 51 to contact respectively the restricting surfaces 714 of the first drive element 71. The flexible end portions 51 are consequently urged to deform inwardly and abut respectively against the abutment surfaces 327, so that rearward movement of the holder 5 relative to the rear end section 312 of the housing unit 3 is limited. When installing a new lancet 10 to the holder 5, the applied force toward the rear end section 312 would not cause an unexpected triggering action of the lancet 10 since the holder 5 is blocked from moving to the trigger position by the abutment surfaces 327. Each of the flexible end portions 51 has a restricting protrusion 511 at a middle thereof for abutting against a respective one of the restricting surfaces 714 and preventing further forward movement of the first drive element 71 relative to the holder 5 that would otherwise hinder the replacement of the needle 11 or even cause separation of the first drive element 71 from the holder 5 when the front end section 311 is removed.

The operation of the blood lancing device 2 to obtain a drop of blood is described in the following. Before use, the length of the portion of the needle 11 extending out of the opening 40 of the cap 4 may be adjusted via rotation of the cap 4.

Figure 6:
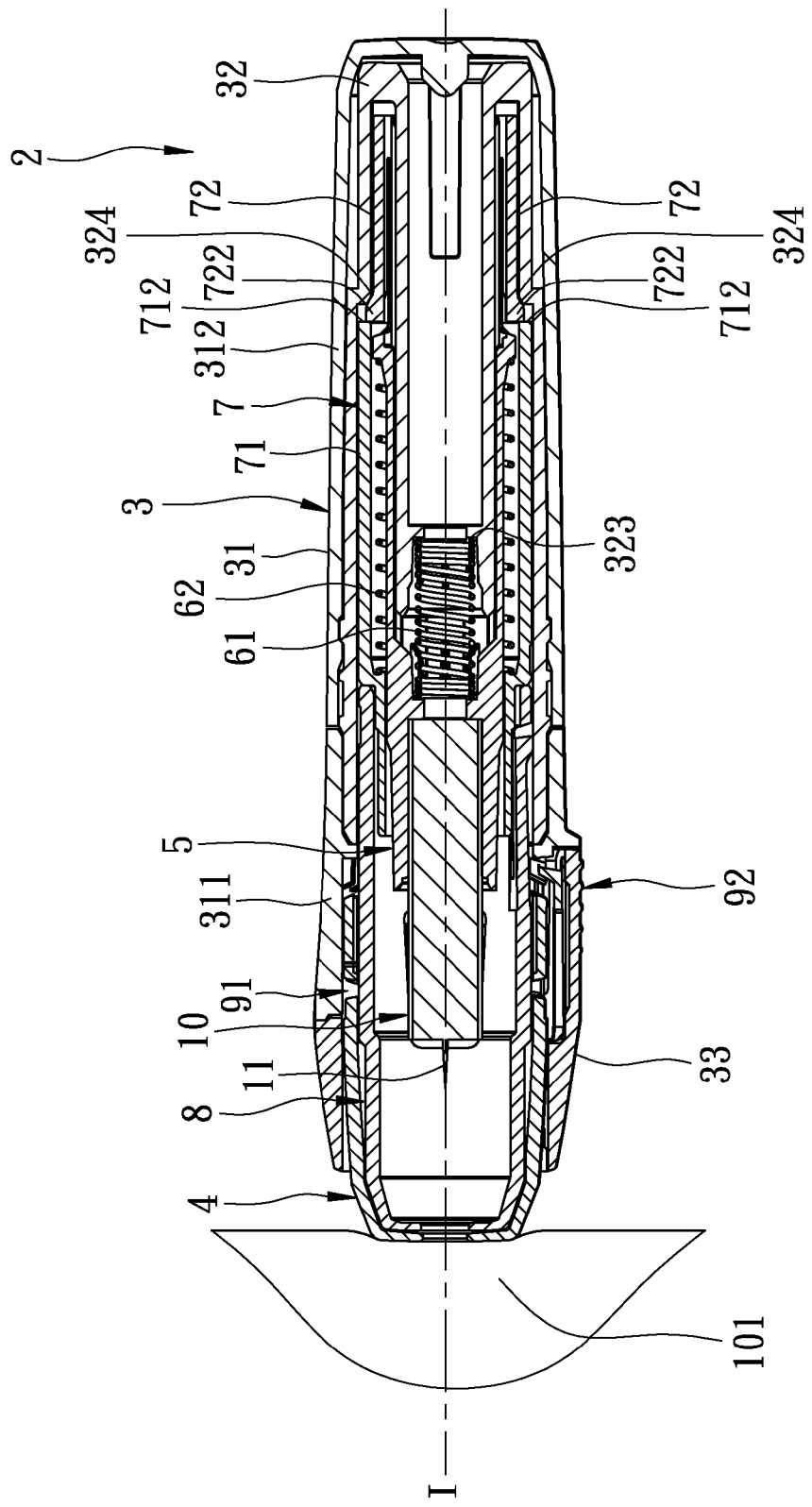
FIG. 6 is another sectional view of the preferred embodiment, illustrating the cap at the retracted position and the holder at a cocking position.

Referring to FIGS. 5, 6 and 7, to use the blood lancing device 2, the front end of the cap 4 is placed on the skin 101, and the pressing lever 922 is pressed to release the sleeve unit 8 from the housing unit 3. At this time, the cap 4 is at the initial position and the holder 5 is at a pre-actuated position. Afterward, with the housing unit 3 being moved toward the skin 101, the cap is pushed from the initial position toward the retracted position, the sleeve unit 8 and the first drive element 71 are driven to move together with the cap 4, the second drive element 72 and the holder 5 are pushed by the limiting surfaces 712 of the first drive element 71 to a cocking position, and the first biasing member 61 is compressed by a backward movement of the holder 5. At this time, the cam blocks 722 of the second drive elements 72 contact respectively the cam surfaces 324 (see FIG. 6). With further backward movement of the holder 5 relative to the housing unit 3 to the trigger position, the second drive elements 72 are deviated from the limiting surfaces 712 so that the holder 5 is fired to the pricking position by the first biasing member 61 while the second biasing member 62 is compressed (see FIG. 7), and immediately be drawn to move rearwardly to a post-actuated position by the second biasing member 62 where the cap 4 is still at the retracted position and the second drive elements 72 are retained by the first drive element 71. Eventually, when the blood lancing device 2 is removed from the skin 101, due to the restoring force of the second biasing member 62, the cap 4 moves back to the initial position, and the first drive element 71 is driven to move forward relative to the holder 5 so that the second drive elements 72 are not urged by the first drive element 71, and forward movements of the second drive elements 72 are limited once again by the limiting surfaces 712 before the next operation of the blood lancing device 2.

To sum up, the blood lancing device of this invention has the following advantages:

1. With the configuration of the transmission assembly 7, the first biasing member 61, and the cam surfaces 324, the blood lancing device 2 could perform a pricking action by simply being placed on and pressed toward the skin 101.

2. By virtue of the second biasing member 62, the cap 4 can be automatically moved from the retracted position to the initial position while the holder 5 can be automatically moved back to the pre-actuated position from the post-actuated position. As a result, the skin pricking operation can be easily repeated.

3. The portion of the needle 11 extending out of the opening 40 of the cap 4 can be adjusted through the adjusting units 91.

4. By virtue of the safety switch 92, an unexpected pricking action of the lancet 10 can be prevented.

5. The positioning member 32 facilitates the interconnection of the front and rear end sections 311, 312 of the housing unit 3 and the assembling of the blood lancing device 2. Moreover, other elements that have various functions may be installed in the blood lancing device 2 easily by virtue of the positioning member 32.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A blood lancing device adapted for pricking a person's skin to obtain a drop of blood, said blood lancing device comprising:

a housing unit including a housing body and a positioning portion that is disposed in said housing body, said housing body having a front end section and a rear end section that is opposite to said front end section along an axis;

a cap projecting forwardly from said housing unit, and movable relative to said housing body along the axis between an initial position and a retracted position, said cap having a front end that is disposed outwardly of said housing unit, that is adapted to be in contact with the skin, and that has an opening;

a lancet;

a holder disposed in said housing unit between said cap and said positioning portion of said housing unit, holding said lancet, and movable along the axis relative to said housing unit between a pricking position whereat said lancet extends outwardly from said opening of said cap, and a trigger position whereat said lancet as a whole is disposed in said housing unit;

a first biasing member disposed between said holder and said positioning portion of said housing unit for biasing said holder to move along the axis away from said positioning portion of said housing unit; and a transmission assembly including a first drive element that is driven to move along the axis relative to said housing unit by said cap, and at least one second drive element that is aligned with said first drive element in the direction of the axis and that has an end connected to said holder such that, when said cap is moved from the initial position toward the retracted position, said second drive element is blocked by said first drive element from forward movement to maintain relative positions of said holder and said first drive element so that said first drive element pushes said holder toward the trigger position and that said second drive element is deviated from said first drive element when said holder reaches said trigger position, thereby allowing for a high speed movement of said holder from the trigger position to the pricking position by virtue of biasing action of said first biasing member, wherein said housing unit further includes an end piece connected to said front end section of said housing body and disposed around said cap, said front end section of said housing body having a stop surface that faces said cap, wherein said blood lancing device further comprises a safety switch that includes a flexible rod connected to and co-movable with said cap and abutting against said stop surface so as to prevent movement of said cap from the initial position to the retracted position, and a pressing lever disposed on said end piece and operable to push said flexible rod to deviate from said stop surface, thereby allowing the movement of said cap from the initial position toward the retracted position.

2. The blood lancing device as claimed in claim 1, further comprising a second biasing member disposed between said holder and said first drive element of said transmission assembly for biasing said holder and said first drive element to move away from each other.

3. The blood lancing device as claimed in claim 2, wherein said front end section and said rear end section of said housing body are interconnected removably, said first drive element of said transmission assembly and said cap being two individual parts, said first drive element being tubular, disposed between said cap and said holder and movable in said housing unit.

4. The blood lancing device as claimed in claim 3, wherein said holder has at least one flexible end portion, and said housing unit further includes at least one abutment surface deviated from said flexible end portion of said holder and positioned such that, when said front end section is removed from said rear end section, said first drive element is biased by said second biasing member to move forward relative to said holder and urge said flexible end portion of said holder to deform inwardly so that rearward movement of said holder relative to said rear end section of said housing unit is limited via abutment of said flexible end portion against said abutment surface to thereby facilitate replacement of said lancet.

5. The blood lancing device as claimed in claim 2, wherein said first drive element has a main body and a limiting surface disposed at an end of said main body for abutting against a corresponding end of said second drive element for blocking the forward movement of said second drive element along the axis relative to said first drive element.

6. The blood lancing device as claimed in claim 5, wherein said second drive element is flexible, said housing unit further including a cam surface, said second drive element being in contact with and urged by said cam surface to deviate from said first drive element when said first drive element pushes said second drive element to the trigger position.

7. The blood lancing device as claimed in claim 2, wherein each of said first drive element, said first biasing member and said holder is at least partially retained in said rear end section of said housing body, and said cap is disposed adjacent to said front end section of said housing body.

8. The blood lancing device as claimed in claim 1, further comprising a stopper disposed between said cap and said first drive element of said transmission assembly, said cap having a front end wall formed with said opening, said stopper having a front end wall formed with an aperture, said lancet including an insert body held by said holder and movable to come into contact with said front end wall of said stopper when said holder is disposed at the pricking position, and a needle mounted fixedly on a front end of said insert body and extending through said opening and said aperture when said holder is disposed at the pricking position, said cap being movable along the axis relative to said stopper to change the distance between said front end walls of said cap and said stopper, thereby adjusting the length of a portion of said needle projecting out of said cap.

9. The blood lancing device as claimed in claim 8, further comprising at least one adjusting unit disposed between said stopper and said cap, said adjusting unit including a guide block that is disposed on said stopper, and a spirally-extending guide slot that is formed in said cap and that is slideably engaged with said guide block, said cap being rotatable relative to said stopper and being movable along the axis relative to said stopper through engagement between said guide block and said guide slot so as to change the distance between said front end walls of said cap and said stopper.

10. The blood lancing device as claimed in claim 9, wherein said adjusting unit further includes an engaging tooth disposed on an outer surface of said stopper, and a plurality of circumferentially arranged positioning grooves formed in an inner surface of said cap, said engaging tooth being engagable with a selected one of said positioning grooves to position said cap relative to said stopper.

11. The blood lancing device as claimed in claim 8, further comprising a second biasing member disposed between said holder and said first drive element of said transmission assembly for biasing said holder and said first drive element to move away from each other.

12. The blood lancing device as claimed in claim 1, wherein said first drive element of said transmission assembly and said cap are two individual parts, said first drive element is tubular and is disposed between said cap and said holder and is movable in said housing unit, said first drive element has a main body and a limiting surface disposed at an end of said main body for abutting against a corresponding end of said second drive element for blocking the forward movement of said second drive element along the axis relative to said first drive element, said second drive element is flexible, said housing unit further includes a cam surface, and said second drive element is in contact with and is urged by said cam surface to deviate from said first drive element when said first drive element pushes said second drive element to the trigger position.

13. The blood lancing device as claimed in claim 12, further comprising a sleeve unit disposed between said cap and said first drive element, said sleeve unit abutting against said first drive element and driven by said cap to move along the axis relative to said housing unit, said sleeve unit including a stopper and a sleeve body respectively proximate to and distal from said cap, said cap having a front end wall that is formed with said opening, said stopper having a front end wall that is contactable with said lancet for preventing further forward movement of said lancet, and an aperture that is formed through said front end wall and that is aligned with said opening of said cap along the axis, said cap being movable relative to said stopper to change the distance between said front end walls of said stopper and said cap.

14. The blood lancing device as claimed in claim 13, wherein said sleeve body and said stopper of said sleeve unit are formed integrally.

15. The blood lancing device as claimed in claim 13, further comprising at least one adjusting unit disposed between said stopper and said cap, said adjusting unit including a guide block that is disposed on said stopper, and a spirally-extending guide slot that is formed in said cap and that is slideably engaged with said guide block, said cap being rotatable relative to said stopper and being movable along the axis relative to said stopper through engagement between said guide block and said guide slot so as to change the distance between said front end walls of said cap and said stopper, an engaging tooth disposed on an outer surface of said stopper, and a plurality of circumferentially arranged positioning grooves formed in an inner surface of said cap, said engaging tooth being engagable with a selected one of said positioning grooves to position said cap relative to said stopper.

16. The blood lancing device as claimed in claim 15, wherein said adjusting unit further includes a window that is formed in said end piece, and a plurality of marks that are disposed on an outer surface of said cap and that correspond respectively to said positioning grooves of said adjusting unit such that rotation of said cap relative to said end piece results in an individual exposure of said marks through said window and adjustment of the length of a portion of said lancet extending outwardly from said opening of said cap when said holder is at the pricking position.

17. The blood lancing device as claimed in claim 16, wherein said safety switch is disposed between said end piece of said housing unit and said sleeve body of said sleeve unit, said flexible rod of said safety switch being connected to and co-movable with said sleeve body and contactable with said stop surface of said front end section of said housing unit proximate to the skin.

18. The blood lancing device as claimed in claim 12, further comprising a second biasing member disposed between said holder and said first drive element for biasing said holder and said first drive element to move away from each other.

19. The blood lancing device as claimed in claim 1, wherein said cap is connected directly to said first drive element of said transmission assembly.

20. The blood lancing device as claimed in claim 19, further comprising a second biasing member disposed between said holder and said first drive element for biasing said holder and said first drive element to move away from each other.

21. The blood lancing device as claimed in claim 19, wherein said second drive element is flexible, and said first drive element has a main body and a limiting surface disposed at an end of said main body for abutting against a corresponding end of said second drive element for blocking the forward movement of said second drive element along the axis relative to said first drive element.

22. The blood lancing device as claimed in claim 21, wherein said housing unit further includes a cam surface, and said second drive element is in contact with and urged by said cam surface to deviate from said first drive element when said first drive element pushes said second drive element to the trigger position.

23. The blood lancing device as claimed in claim 19, wherein said front end section and said rear end section of said housing body are interconnected removably, said holder has at least one flexible end portion, and said housing unit further includes at least one abutment surface deviated from said flexible end portion of said holder and positioned such that, when said front end section is removed from said rear end section, said first drive element is biased by said second biasing member to move forward relative to said holder and urge said flexible end portion of said holder to deform inwardly so that rearward movement of said holder relative to said rear end section of said housing unit is limited via abutment of said flexible end portion against said abutment surface to thereby facilitate replacement of said lancet.

* * * * *